United States Patent [19]
Hagen

[11] Patent Number: 4,735,618
[45] Date of Patent: Apr. 5, 1988

[54] PROTECTIVE ENCLOSURE FOR HYPODERMIC SYRINGE

[75] Inventor: John Hagen, Morton Grove, Ill.

[73] Assignee: Henry E. Szachowicz, Jr., Morton Grove, Ill. ; a part interest

[21] Appl. No.: 75,532

[22] Filed: Jul. 20, 1987

[51] Int. Cl.⁴ ............................................. A61M 5/32
[52] U.S. Cl. .................................... 604/192; 604/198; 604/110
[58] Field of Search ............... 604/110, 111, 117, 192, 604/187, 197, 198, 263, 163

[56] References Cited
U.S. PATENT DOCUMENTS

| | | | |
|---|---|---|---|
| 3,840,008 | 10/1974 | Noiles | 604/117 X |
| 4,139,009 | 2/1979 | Alvarez | 604/198 |
| 4,266,543 | 5/1981 | Blum | 604/263 X |
| 4,681,567 | 7/1987 | Masters et al. | 604/198 |

Primary Examiner—John D. Yasko
Attorney, Agent, or Firm—Basil E. Demeur; Robert E. Knechtel; Alan B. Samlan

[57] ABSTRACT

There is disclosed a protective enclosure for hypodermic syringe needle formed by a tubular sleeve sized for friction fitting engagement over the barrel portion of the syringe, a needle guard portion at the opposed end thereof. The needle guard including a central needle channel traversing the same, and the needle guard being spaced from the tubular sleeve a distance such that the tip end of the syringe needle lies within the confines of the central needle channel in a normal resting position thereof. The sleeve and needle guard are connected by two pair of pivotally movable arms which operate to permit the needle to pass through the central channel during injection, and rest in a needle pocket when injection has been completed.

9 Claims, 2 Drawing Sheets

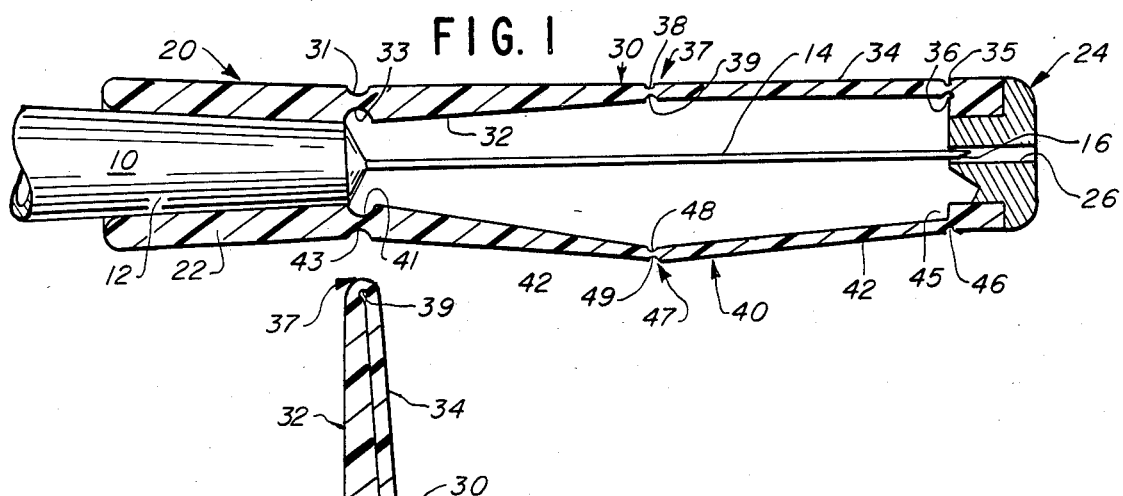
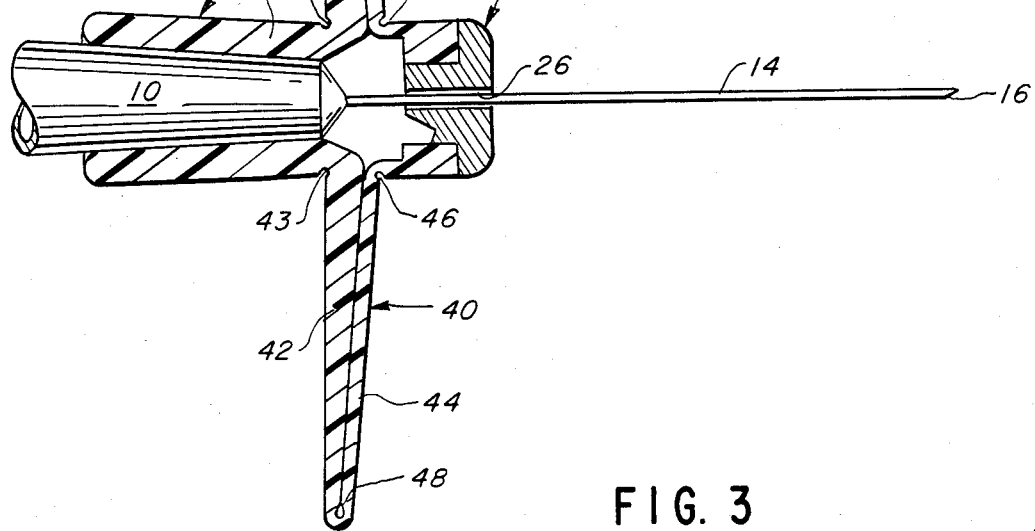
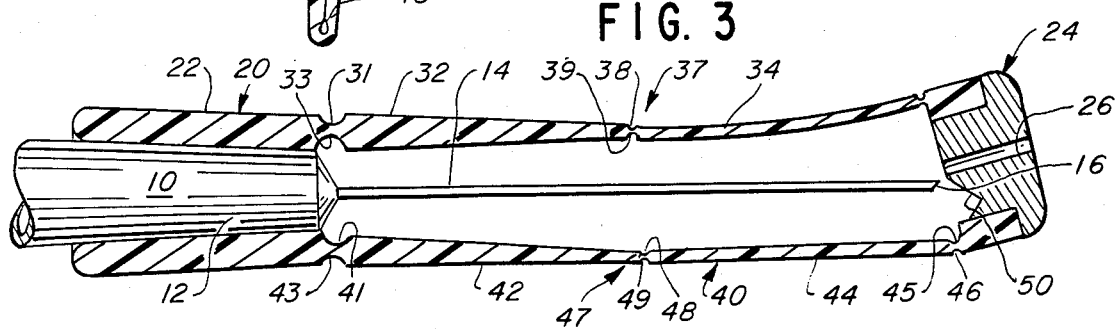
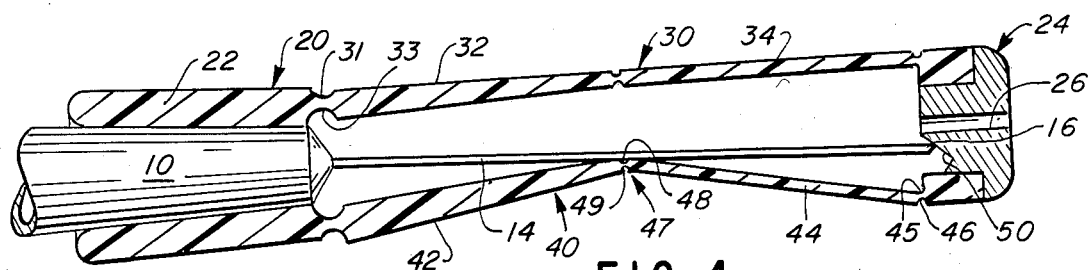

FIG. 5
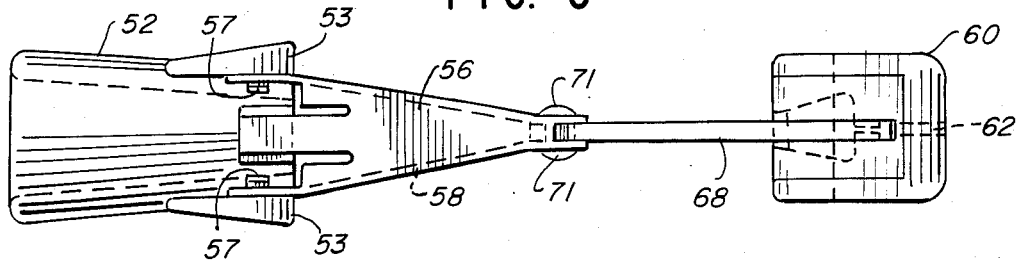
FIG. 6
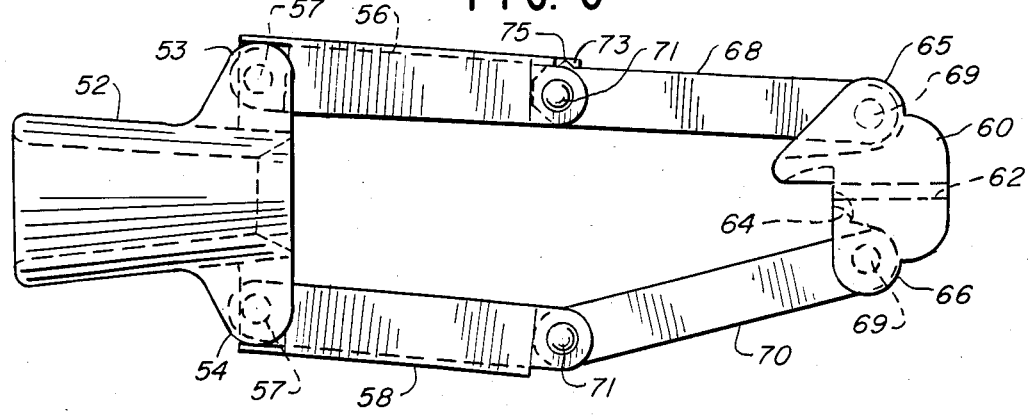
FIG. 7

PROTECTIVE ENCLOSURE FOR HYPODERMIC SYRINGE

BACKGROUND OF THE INVENTION

The art field with respect to protective devices for syringe needles has become quite active in the recent past. The recognition of the variety of disease which are inflicted upon users of hypodermic syringes, including patients as well as hospital personnel, has become a subject of great concern. This is especially true in view of the threat to life diseases such as Acquired Immune Deficiency Syndrome (AIDS) as well as other diseases such as hepatitis and the like as opposed to users of hypodermic syringes. The problems which have arisen in hospitals relate in great measure to the personnel including doctors and nurses who are required to given injections and ensure that they do not puncture themselves unintentionally. However, the problem of unintended puncture wounds is a serious problem and in this connection, the art has searched for protective devices which may be easily and effectively used by hospital personnel to ensure that once an injection has been given, that the operator does not unintentionally puncture themselves while attempting to dispose of the syringe.

Insofar as the patented art is concerned, various devices have been developed with a view toward permitting the operator to insert a protective shield over the syringe needle once the injection process has been completed. For example, U.S. Pat. No. 4,559,042 shows a safety enclosure for a disposable hypodermic syringe needle which is basically formed by an elongated tubular enclosure having a radially outwardly extending shield formed at the insertion end of the device. The intention is that once the needle has been utilized, the operator grasps the elongated tubular portion and slides the same over the needle with the radial shield allegedly protecting the operator against unintended puncture wounds should the operator not properly insert the needle within the confines of the tubular sleeve. The same is true with respect to the device shown in U.S. Pat. No. 4,573,975 which again is a tubular sleeve having an umbrella type shield formed thereon such that the operator's hand is protected when the operator attempts to insert the needle into the elongate tube.

U.S. Pat. No. 3,658,061 shows another version of a needle guard which is utilized by fitting the base of the guard over the barrel end of the syringe needle, and after use, guard means consisting of a tubular sleeve snapped over the entire length of the needle in snug relationship thereby to fully encase the needle and thereby protect the operator against unintended puncture wounds.

Another format for a protective device for a hypodermic syringe is shown in U.S. Pat. No. 2,854,976 wherein the protective device is formed by a portion which is intended to snap onto the barrel portion of the syringe, and includes an outwardly extended cylindrical portion intended to protect the point end of the needle. However, it is noted that in this case, the protective device is intended to protect the needle against damage prior to use, rather than in protecting the operator from unintended puncture wounds after use, and it is quite apparent that the protective device disclosed therein is intended to be removed incident to the use of the needle for the injection process, and reinserting the protector subsequent to use. However, it is believed that during the process of reinserting the protector after use, unintended puncture wounds may still occur, and therefore, a device of the type shown therein has not been particularly commercially applicable for protecting operators against unintended puncture wounds.

Still another version of a protective device for a hypodermic needle is shown in U.S. Pat. No. 4,139,009, wherein the protective device is a retractible covering means for the forward portion of the needle and is intended to keep the needle firmly nestled in a protective tip end prior to use, and subsequent to use by causing the retractible means to envelop the needle after use. The device as depicted therein is intended to have bowable arms which normally biasingly urge the tip protector back into its overlying relationship with respect to the needle when the needle is retracted from the patient following the injection process.

An older version of a protective shield is shown in U.S. Pat. No. 3,134,380, which shows a bellows type structure enveloping the needle and being retractible such that the needle may be exposed for the injection process, with the bellows then being urged to cover the needle upon completion of the injection process.

Various other patents exist which show other versions of protective devices, generally the device is showing a structure which is intended to normally biasingly urge a protective shield or cover back over the needle once the injection process has been completed. However, it has been noted that in many of these devices, the needles do not always properly align with the channels in the nose guards, and therefore, none of these devices has achieved any degree of commercial success. Furthermore, none of the devices known to date are provided with any type of needle tip and capture pockets such that upon completion of the injection process, the protective enclosure may be manipulated to capture the needle tip end, and prevent any possibility of the tip end puncturing the operator subsequent to the injection process.

The intent of the present invention is to provide an improved protective enclosure for use in conjunction with hypodermic syringe needles which permits the operator to easily and efficiently manipulate the protective enclosure with a high degree of surety, and enclose the tip end of the syringe needle subsequent to the injection process such that the operator is not required to manipulate, to any great degree, the protective device in order to capture the tip end of the needle and prevent unintended puncture wounds.

OBJECTS AND ADVANTAGES

It is therefore the principal object of the present invention to provide an improved protective enclosure for use in conjunction with hypodermic syringe needles which minimizes the degree of manipulation required in order to shield the syringe needle prior to as well as subsequent to the injection process, in order to prevent unintended puncture wounds.

In conjunction with the foregoing, the principal object of the present invention is to provide a protective enclosure for hypodermic syringe needles of the type having a barrel portion and a hypodermic needle with a puncture tip end extending outwardly therefrom, the improved protective device formed by tubular sleeves sized for friction fitting engagement over the barrel portion of the hypodermic syringe, a needle guard positioned at the opposed end of the protective enclosure, the needle guard being substantially solid and having a central needle channel traversing the needle guard, said needle guard being spaced from the tubular sleeve a distance such that the tip end of the syringe needle lies within the confines of the central needle channel and the normal resting position of the protective enclosure, a pair of opposed connecting arms, each of the arms having one end pivotally secured to the tubular sleeve and the opposed end pivotally secured to the needle guard being designed to normally biasingly urge the needle guard in space relation with respect to the tubular sleeve, each of the arms having a centrally positioned hinge joint such that the arms are pivotally movable at the hinge joint, one of the arms having an overall length exceeding the length of the opposed arm such that the arm is an elongate arm and is normally bowed outwardly at the hinge joint thereof away from the opposed arm in the normal resting position of the protective enclosure, the needle guard being movable toward the tubular sleeve as the arms are pivoted at the respective hinge joints away from each other thereby to allow the syringe needle to pass through the central needle channel and extend outwardly from the protective enclosure to allow for the injection process, and the arms biasingly urging the needle guard into spaced relation away from the tubular sleeve upon completion of the injection process with the syringe needle once again coming to rest within the confines of the needle channel in order to shield the syringe needle and prevent unintended needle punctures to the operator.

In conjunction with the foregoing object, it is a further object to provide an improved protective enclosure for a syringe needle of the type described, wherein the needle guard is further provided with a needle pocket formed therein adjacent the centrally disposed needle channel and in adjacent alignment with the elongate arm such that the movement of the elongate arm at the hinge joint in the direction of the opposed arm cocks the needle guard to release the tip end of the syringe needle from the central needle channel and position the syringe needle into alignment with the needle pocket such that continued movement of the elongate arm in the direction of the opposed arm captures the syringe needle in the needle pocket and prevents any further usage of the syringe needle and unintended needle punctures to the user thereof.

In conjunction with the foregoing objects, it is a further object of the present invention to provide a protective enclosure of the type described wherein the entire protective enclosure may be formed of a thermal plastic resin material and may be unitary in construction.

Still a further object of the present invention is to an improved protective enclosure for a syringe needle of the type described wherein the protective enclosure may be formed from a metallic material.

In conjunction with the foregoing object, a further object of the present invention is to provide an improved protective enclosure for a hypodermic syringe wherein each of the pair of connecting arms is formed by a sleeve armed pivotally connected to the tubular sleeve at one end and extending outwardly therefrom to an outer end and a guard arm pivotally connected to the needle guard at one end and extending inwardly toward the sleeve arm to an inner end, the outer end of the sleeve arm and the inner end of the guard arm being pivotally connected together in a central portion thereof whereby the arms are each pivotally movable with respect to the tubular sleeve and the needle guard and are each pivotally movable along the central portion thereof with respect to each other.

In conjunction with the foregoing object, it is a further object of the invention to provide the improved protective enclosure for a hypodermic syringe of the type described wherein the elongate arm is formed by providing one guard arm having a length exceeding the length of th eoppsed guard arm such that the overall length of one connecting arm formed by a sleeve arm and a guard arm exceeds the overall length of the opposed connecting arm and is normally bowed outwardly away from the opposed connecting arm.

Further features of the invention pertain to the particular arrangement of the parts and elements whereby the above-outlined and additional operating features thereof are attained.

The invention, both as to its organization and method of operation, together with further objects and advantages thereof, will best be understood by reference to the following specification taken in connection with the accompanying drawings.

SUMMARY OF THE INVENTION

In summary, the present invention is intended to provide a further improved protective enclosure for a hypodermic syringe of the type including a barrel portion and a puncture needle extending outwardly therefrom, the protective enclosure retrofitting existing hypodermic syringe needles prior to use, and being manipulable in order to leave the protective enclosure in place during the injection process, and insuring that the tip end of the needle will be shielded subsequent to the injection process to prevent unintended puncture wounds to the operator. The improved protective enclosure of the present invention is further provided with a needle pocket positioned in the needle guard end of the device for the purpose of permitting the operator to capture the tip end of the syringe needle subsequent to the injection process to ensure that the syringe cannot be re-used, and that the tip end is firmly captured within the needle guard portion of the device hence prevent any unintended puncture wounds. The particular arrangement of the arms which operate the needle guard relative to the tubular sleeve are such that the degree of assurance that the syringe needle will be captured within the confines of the needle channel both during and subsequent to the use is greatly enhanced, and that the provision of the needle pocket will absolutely ensure the operator that with a simple physical manipulation, the tip end of the needle may be captured and prevent any further possibility of a puncture wound.

BRIEF DESCRIPTION OF THE DRAWINGS

FIG. 1 is a side elevational view, partly in cross section, showing the protective enclosure as fitted over the hypodermic syringe needle in its resting position;

FIG. 2 is a side elevational view, partly in cross section, showing the protective enclosure moved to the fully retracted position thereby to expose the hypodermic syringe needle incident to the injection process;

FIG. 3 is a side elevational view, partly in cross section, showing the protective enclosure with elongate arm manipulated partway toward the opposed arm and the needle guard in its cocked position with the needle pocket coming into horizontal alignment with the tip end of the syringe needle;

FIG. 4 is a side elevational view, partly in cross section, showing the elongate arm fully cocked thereby to position the tip end of the syringe needle into the needle pocket of the needle guard;

FIG. 5 is a side elevational view, partly in cross section, showing an alternate embodiment of the subject protective enclosure formulated of a metallic material wherein the connecting arms are secured by hinge rivets to the tubular sleeve at one end and the needle guard at the opposed end and also interconnected by hinge rivets in the central portion thereof;

FIG. 6 is a top plan view showing the embodiment as depicted in FIG. 5, illustrating the manner in which the elongate arm is constructed relative to the opposed connecting arm with the protective enclosure in its normal resting position; and FIG. 7 is a side elevational view taken from the side opposed to the view depicted in FIG. 5, showing the subject protective enclosure in its rest position.

DETAILED DESCRIPTION OF THE DRAWINGS

For ease of description, the embodiment as depicted in FIGS. 1 through 4 of the drawings will be described, since it represents the embodiment which is formulated of a thermal plastic resin material, is unitary in construction, and represents the most simplified version of the invention described and claimed herein.

With specific reference to FIG. 1 of the drawings, there is shown a hypodermic syringe needle 10 which includes a barrel portion 12 and a hypodermic syringe needle 14 having a puncture tip end 60. As shown therein, the hypodermic syringe 10 is shown to be enclosed by the protective enclosure generally depicted by the numeral 20. The protective enclosure 20 is formed by a tubular sleeve 22 which is sized to friction fittingly engage over the barrel portion 12 of the hypodermic syringe 10. The opposed end of the protective enclosure 20 includes a needle guard 24 which is further provided with a centrally positioned needle channel 26 which accommodates the syringe needle 14 therethrough. The tubular sleeve 22 and needle guard 24 are interconnected by means of a pair of opposed connecting arms 30 and 40 respectively. As shown in FIGS. 1 through 4 of the drawings, the first connecting arm 30 is shown to be formed integrally with the tubular sleeve 22, and is formed by a first sleeve arm 32 which is pivotally connected to the tubular sleeve 22 by means of a pair of upper and lower detents 31 and 33 respectively. The connecting arm 30 is completed by means of a first guard arm 34 which is pivotally connected to the needle guard 24 by means of a pair of upper and lower detents 35 and 36 respectively, such that the first guard arm 34 is similarly pivotally interconnected with the needle guard 24. The first sleeve arm 32 and first guard arm 34 are interconnected, and include a central hinge joint 37 formed by an upper detente 38 and a lower detent 39.

As shown in FIG. 2 of the drawings, when the needle guard 24 is manipulated by forcing the same in the direction of the tubular sleeve 22, the connecting arm 30 is designed to be pivotally movable with respect to the needle guard 24 by means of the upper detent 35 innerconnecting the first guard arm 34 with the needle guard 24, and with respect to the tubular sleeve 22 by means of the upper detent 31, innerconnecting the first sleeve arm 32 with the tubular sleeve 22, with the central hinge joint being pivotally movable by means of the lower detent 39 from the central hinge joint 37. In this posture, the syringe needle 14 has traversed and moved through the needle channel 26 thereby to expose the tip end 16 incident to the injection process.

It will also be appreciated that the lower connecting arm 40 is similarly constructed in that it is formed by means of a first sleeve arm 42 and a first guard arm 44, the first sleeve arm 442 being innerconnected to the tubular sleeve and having an upper detent 41 and a lower detent 43 such that a pivotal joint is created, while the first guard arm 42 is similarly innerconnected with the needle guard 24 and includes an upper detent 45 and a lower detent 46 thereby to create a pivotal connection thereat. The first sleeve arm 42 and first guard arm 44 are joined at a central hinge joint 47 which again includes an upper detent 48 and a lower detent 49 thereby to create a hinge joint at that point.

Once again, as illustrated in FIG. 2 of the drawings, the movement of the needle guard 24 in the direction of the tubular sleeve 22 will cause the respective upper and lower connecting arms to pivotally move into the position as depicted in FIG. 2, whereby the needle 14 is exposed in order to permit the tip end 16 of the needle to be available for the injection process.

Upon completion of the injection process, the thermal plastic resin material of which the protective enclosure 20 is formulated biasingly urges the needle guard 24 away from the tubular sleeve 22 into its rest position as generally shown in FIG. 1, such that the tip end 16 of the needle 14 will rest, once again, in the needle channel 26.

The present invention contemplates a further improvement in that the needle guard 24 is shown to be further provided with a needle pocket 50 which functions to capture the tip end 16 of the needle 14 when the connecting arms 30 and 40 respectively are manipulated properly. As particularly shown in FIGS. 3 and 4 of the drawings, the connecting arm 40 has an overall length exceeding the overall length of connecting arm 30 in that the first guard arm 44 of the connecting arm 40 has a length greater than the first guard arm 34 of the connecting arm 30 which thereby causes the connecting arm 40 to bow away from the connecting arm 30 in the normal resting position as shown in FIG. 1. When the connecting arm 40 is manipulated by applying pressure to the central hinge joint 47 thereby to push the connecting arm 40 toward the connecting arm 30 as shown in FIG. 3, the needle guard 24 is caused to cock upwardly such that the tip end 16 of the needle 14 pulls inwardly from the needle channel 26, and commences to align with the needle pocket 50. As the connecting arm 40 is pushed upwardly against the needle 14 (see FIG. 4) the needle pocket 50 will capture the tip end 16 of the needle 14 therein. In this manner, a positive locking of the needle within the confines of the needle guard 24 is accomplished by securing the tip end 16 of the needle 14 in the needle pocket 50. This prevents any subsequent re-use of the needle, and also positively prevents any unintended needle puncturing by the operator incident to the use of the needle. It will therefore be appreciated that once the injection process has been completed (see FIG. 2), and as the needle guard 24 is biasingly urged to its rest position as shown in FIG. 1 of the drawings, the operator need only manipulate the lower connecting arm 40 by pressing it in the direction of the needle 14 thereby to cock the needle guard 24 into its capturing position until the needle pocket 50 captures the tip end of the needle 16 and hence prevent any unintended needle puncture wounds to the operator. It will also be apparent that at no time is the guard removed from the needle nor is the operator required to attempt to insert any type of protective sleeve or other casing over the needle once the injection process has been completed. The capturing of the needle tip into the needle pocket is completed virtually automatically.

Insofar as the embodiment shown in FIGS. 5, 6 and 7 of the drawings, this embodiment contemplates that the protective enclosure 60 is formulated from a metallic material. the essence of the invention, regardless of which embodiment is described, is considered to be identical, and in that connection, the following description is presented merely for the purpose of identifying the construction of the metallic embodiment of the subject invention.

With respect to FIGS. 5 and 6 of the drawings, the metallic embodiment of the invention is depicted. It will be observed that the device is generally configured the same as the embodiment shown in FIGS. 1 through 4 of the drawings, the only difference being that the present embodiment is not formulated from a single piece of metal. In terms of structure, it will be noted that with respect to FIG. 6, the device is constructed from a tubular sleeve 52 which is designed to frictionally engage the barrel portion of a hypodermic syringe. The tubular sleeve 52 includes a pair of outstanding ears 53 and 54 respectively to which the upper and lower sleeve arms 56 and 58 respectively are connected. It will be noted that the connection of the sleeve arms 56 and 58 to the ears 53 and 54 is accomplished by means of a pair of rivet pins 57. The opposed end of the protective enclosure is provided with a needle guard 60 which includes a needle channel 62 traversing the center section thereof. The metallic embodiment is also provided with a needle pocket 64 which functions similarly to the needle pocket 50 in connection with the protective enclosure 20 depicted in FIGS. 1 through 4 of the drawings. The needle guard 60 is also provided with a pair of mounting ears 65 and 66 respectively in order to accommodate the mounting of the upper and lower guard arms 68 and 70 respectively. Once again, the guard arms 68 and 70 are mounted to the mounting ears 65 and 66 by a pair of rivet pins 69 thereby to accommodate the pivotal rotation of the arms 68 and 70 relative to the needle guard 60.

It will be noted that the respective sleeve arms 56 and 58 are connected to the respective guard arms 68 and 70 by means of rivet pins 71 in order to achieve pivotal connection therebetween. Hence, as an overall structure, the tubular sleeve 52 is connected therefore to the needle guard 60 by means of the innerconnecting of the arms 56 and 68 and 58 and 70 respectively.

It will also be noted that the lower guard arm 70 has an overall length exceeding the length of the upper guard arm 68, such that the sleeve arm 58 when connected to the guard arm 70 is bowed out and away from the upper arms 56 and 68 respectively. It will be apparent from a comparison of FIGS. 1 and 4 of the drawings, that as the lower arms 58 and 70 are moved toward the upper arms 56 and 68 respectively, the needle guard 60 is caused to cock upwardly thereby to permit the tip end 16 of the needle 14 to withdraw from the needle channel 62, and be captured by the needle pocket 64 as the arms 58 and 70 are continuously forced upwardly. Hence, the functional result as depicted in FIGS. 3 and 4 of the drawings is achieved with the metallic version of the embodiment in the present invention as well.

In addition, with respect to FIG. 6 of the drawings, it will be noted that the upper sleeve arm 56 and upper guard arm 68 are further provided with a locking mechanism. It will be observed that the upper sleeve arm 56 is provided with an aperture 73 adjacent the outer end thereof, while the upper guard arm 68 is provided with a nib 75 upstanding therefrom. In the normal resting position as shown in FIG. 6 of the drawings, the nib 75 seats into the aperture 73 thereby locking the arms in position. It will be noted that nib 75 has slight chamfer to it along the forward portion thereof such that when the lower arms 58 and 70 are squeezed toward the upper arms 56 and 58, the nib 75 may easily move out of the aperture 73 for a short distance. Upon completion of the squeezing process incident to capturing the needle pocket 64, the upper arms 56 and 68 respectively will come back to substantially straight line position with the nib 75 locked into the aperture 73. This provides a locking feature in order to prevent any possibility of the needle escaping from the needle pocket 64 as a result of any possible misalignment of the upper arms 56 and 68. Hence, the locking mechanism functions for the dual purpose of making sure that the upper arms 56 and 68 align properly, and locking the same in position once the needle has been captured in the needle pocket 64.

With respect to FIGS. 5 and 7 of the drawings, these figures represent side elevational views of the subject embodiment, and it will be noted that in this embodiment, the respective sleeve arms 56 and 58 are mounted angularly with respect to the tubular sleeve 52. Such mounting is considered to be a matter of engineering only, and has no particular effect on the operation of the subject device.

In terms of materials, it is contemplated that each of the embodiments as disclosed herein is intended to be a disposable item, and therefore, the thermal plastic resin material utilized in connection with the embodiment depicted in FIGS. 1 through 4 of the drawings should be selected with the view that disposability is desirable. Furthermore, the plastic should also have a natural biasing characteristic, so that the material has a natural tendency to biasingly urge the needle guard 24 in spaced away relationship with respect to the tubular sleeve 20. Hence, it is contemplated that material such as nylon, polyethylene, and similar such plastics would be suitable materials. In connection with the metallic version, once again, it is contemplated that the device is to be disposable, therefore inexpensive alloys are considered to be suitable for constructing the elements incident to creating the device. Other metals which may be utilized include steel, stainless steel, brass, copper and other such metals as may be appropriate or econimically available. For example, aluminum alloys tend to be readily available at economically reasonable prices in order to make the device truly disposable.

It is also considered to be within the scope of the present invention to construct the protective enclosure of the present invention as integrally molded to the barrel portion 12 of the hypodermic syringe 10. Hence, with respect to the embodiments depicted in FIGS. 1 through 4 of the drawings, it is possible that the tubular sleeve 22 could actually be molded integrally with the barrel portion 12 such that the entire protective device would be integrally secured to the hypodermic syringe needle 10. The feasibility of a unitary construction would be a matter of economic feasibility of the construction of the molds which would be capable of molding the entire device. This is, however, not considered to be the essence of the present invention which is the provision of a protective enclosure for syringe needle which functions in the manner described hereinabove.

From the foregoing description, it is clear that the protective enclosure for hypodermic syringe needles of the type described and claimed herein will function ideally for the purpose intended. The subject protective enclosure will in fact function to shield the hypodermic syringe needle at all times prior to the injection process, but will nevertheless permit the needle to be exposed for the injection process, after which the needle may be captured with a simple manipulation of the device, without the need of having to encase the needle with a separate protective enclosure of the types generally known in the prior art. Hence, the device may be easily utilized without any undue manipulation, the device merely requiring a simple pressure manipulation to move the arms toward each other in order to positively capture the needle and prevent undue puncture wounds.

While there has been described what is at present considered to be the preferred embodiment of the invention, it will be understood that various modifications may be made therein and is intended to cover in the appended claims all such modifications as fall within the true spirit and scope of the invention.

I claim:

1. A protective enclosure for use in conjunction with a hypodermic syringe of the type having a barrel portion and a hypodermic needle with a punctured tip end extending outwardly therefrom, the improvement comprising in combination, a tubular sleeve sized for friction-fitting engagement over the barrel portion of the hypodermic syringe, a needle guard positioned at the opposed end of said protective enclosure, said needle guard being substantially solid and having a central needle channel traversing said needle guard, said needle guard being spaced from said tubular sleeve a distance such that the tip end of the syringe needle lies within the confines of said central needle channel in the normal resting position of said protective enclosure, a pair of opposed connecting arms, each of said arms having one end fixedly secured to said tubular sleeve and the opposed end secured to said needle guard and being designed to normally biasingly urge said needle guard in spaced relation to said tubular sleeve, each of said arms having a centrally positioned hinge joint such that said arms are pivotally movable at said hinge joint, one of said arms having an overall length exceeding the length of said opposed arms such that said arm is an elongate arm and is normally bowed outwardly at the hinge joint thereof away from said opposed arm in the normal resting position of said protective enclosure, said needle guard being movable toward said tubular sleeve as said arms are pivoted at said respective hinge joints thereby to allow the syringe needle to pass through said central needle channel and extend outwardly from said protective enclosure to allow for the injection process, and said arms biasingly urging said needle guard into spaced relation away from said tubular sleeve upon completion of the injection process with the syringe needle once again coming to rest within the confines of said needle channel thereby to shield said syringe needle and prevent unintended needle punctures to the operator thereof.

2. The protective enclosure as set forth in claim 1 above, wherein said needle guard is further provided with a needle pocket formed therein adjacent the centrally disposed needle channel and in adjacent alignment with said elongate arm, such that the movement of said elongate arm at the hinged joint thereof in the direction of said opposed arm cocks said needle guard to release the tip end of the syringe needle from said central needle channel and positions the syringe needle into alignment with said needle pocket, and continued movement of said elongate arm in the direction of said opposed arm captures the tip end of the syringe needle in said needle pocket thereby to prevent further usage of said syringe and prevent unintended needle punctures to the operator thereof.

3. The protective enclosure as set forth in claim 2 above, wherein said protective enclosure is formed from a thermal plastic resin material.

4. The protective enclosure as set forth in claim 3 above, wherein said tubular sleeve, needle guard, and opposed arms are of unitary construction and each of said hinge joints is formed by detense formed in said connecting arms.

5. The protective enclosure as set forth in claim 4 above, wherein said needle guard comprises a pair of opposed connecting arm extension portions and a rubber needle guard plug which includes said central needle channel and said needle pocket, fixedly secured between said arm extension portions.

6. The protective enclosure as set forth in claim 1 above, wherein said protective enclosure, including said tubular sleeve, connecting arms and needle guard is formed from a metallic material.

7. The protective enclosure as set forth in claim 6 above, wherein each of said pair of connecting arms is formed by a sleeve arm pivotally connected to said tubular sleeve at one end and extending outwardly therefrom to an outer end, and a guard arm pivotally connected to said needle guard at one end and extending inwardly toward said sleeve arm to an inner end, said outer end of said sleeve arm and said inner end of said guard arm being pivotally connected together in a central portion thereof, whereby said arms are each pivotally movable with respect to said tubular sleeve and said needle guard, and are each pivotally movable along the central portion thereof.

8. The protective enclosure as set forth in claim 7 above, wherein each of said pivotal connections is formed by a hinge rivet thereby to innerconnect said tubular sleeve and needle guard via said connecting arms, and said connecting arms being pivotally connected in the central portion thereof by means of a hinge rivet.

9. The protective enclosure as set forth in claim 7 above, wherein said elongate arm is formed by providing one guard arm having a length exceeding the opposed guard arm such that the overall length of one connecting arm formed by a sleeve arm and a guard arm exceeds the overall length of the opposed connecting arm, and is normally bowed outwardly away from said opposed connecting arm.

* * * * *